(12) United States Patent
Maimets

(10) Patent No.: US 6,585,709 B2
(45) Date of Patent: Jul. 1, 2003

(54) APPARATUS AND METHOD FOR PATIENT CARE AND CLEANING

(75) Inventor: Lembit Maimets, Richmond Hill (CA)

(73) Assignee: Baltic Trader Limited, Ontario (CA)

( * ) Notice: Subject to any disclaimer, the term of this patent is extended or adjusted under 35 U.S.C. 154(b) by 164 days.

(21) Appl. No.: 09/878,294

(22) Filed: Jun. 12, 2001

(65) Prior Publication Data

US 2002/0010446 A1 Jan. 24, 2002

Related U.S. Application Data

(60) Provisional application No. 60/210,828, filed on Jun. 12, 2000.

(51) Int. Cl.[7] .................................................. A61F 5/44

(52) U.S. Cl. ........................ 604/355; 604/326; 604/327

(58) Field of Search ................................ 604/355, 327, 604/331, 345, 320, 317, 318, 319, 321, 322, 326, 343, 352

(56) References Cited

U.S. PATENT DOCUMENTS 5,342,583 A  8/1994  Son ............................ 422/107
5,681,297 A  10/1997  Hashimoto et al. ......... 604/355

Primary Examiner—Weilun Lo
Assistant Examiner—Jacqueline F Stephens
(74) Attorney, Agent, or Firm—Greenblum & Bernstein, P.L.C.

(57) ABSTRACT

An apparatus and method for patient care and cleaning. Included are semi-disposable pants, a mattress, a care materials inflow preparation unit, a waste fluid container, a control unit, and a remote control device. The body area to be washed is covered with pants, providing a soft container having fittings connecting it to a wash liquid supply and effluent disposal hoses. The waist and femoral regions of the pants are provided with sealing rings for sealing of the space inside the pants during waste handling cycles of the patient care, and unsealing when this cycle is completed. Sensors are located in the pants for remote control of all materials handling functions in the patient care process. The mattress is provided with inflatable chambers that facilitate positioning of the patient's body and creation of a hollow space for bath water, thereby facilitating in-bed bathing of the entire body.

18 Claims, 12 Drawing Sheets

APPARATUS AND METHOD FOR PATIENT CARE AND CLEANING

CROSS-REFERENCE TO RELATED APPLICATION

This application is based upon U.S. Patent Application No. 60/210,828, filed on Jun. 12, 2000, the disclosure of which is hereby incorporated-by-reference thereto in its entirety and the priority of which is claimed under 35 USC 119(e).

BACKGROUND OF THE INVENTION

1. Field of the Invention

The present invention relates to an apparatus and method for patient care and cleaning. More particularly, the invention is related to an apparatus and method for managing the waste from a patient during care, maintenance, and treatment of sick or handicapped persons, which minimizes or eliminates the need for contact by the care giving personnel with the body waste products of the patient.

2. Description of Background and Relevant Information

A large number of patients are unable to transport themselves to conventional toilet facilities when the need arises. Often a care giver is not available at a critical time. When such patients suffer an episode of excretory functions, they may remain for a relatively prolonged period of time in contact with the waste products. In addition to being embarrassing to the patient, the waste products can cause skin maceration and breakdown as well as urinary tract infections. Moreover, cleaning and drying of the patient can require up to 45 minutes or more of nursing time after each such episode. A single nurse is often incapable of turning the patient to the position needed for treatment or comfort. Thus, more often than one nurse must be involved in the patient care.

A device such as disclosed in U.S. Pat. No. 5,681,297 including a diaper cap having a main body for encompassing parts of the hip and buttocks region of the human body lacks a number of necessary functions. For example, there is a sealing problem between excreted waste and the patient's clothes and bed. Also, there exists the problem of limited washing and drying cycles, because the above-mentioned device does not allow for a possibility of passing wash water and drying air to narrow spaces at the extremities of the device between covered and uncovered areas of the patient's body and the device.

A device such as disclosed in U.S. Pat. No. 5,342,583 is composed of a wearing section, a disposal device installed in an aperture in the wearing section, a washing device incorporated in the disposal device, and a driving section for operating the device. This device has a number of disadvantages. For example, wash water and excrement tends to leak out through the periphery of the pressing tube as a result of the poor adhesiveness of the pressing tube to the patient's body. This poor adhesiveness results from difficulty in fitting the device to various body shapes unless prohibitively high pressure is applied to the body part to form the seal. Such pressure would stop blood circulation in a patient with low venal pressure.

SUMMARY OF THE INVENTION

The present invention is intended to solve the above-described difficulties and disadvantages of the prior art.

More specifically, it is an object of the invention to provide an apparatus that is easy to fit onto various body shapes, that provides an improved washing, drying, and other amenities and treatment functions needed for the care, comfort, and well-being of the patient.

It is a further object of the invention to minimize or eliminate altogether the requirement for personal contact by the patient care giver with bodily waste products of the patient.

An additional object of the invention is to provide an apparatus having a built-in option enabling a mentally aware patient to assist oneself without being exposed to the scrutiny of others in an embarrassing situation. Generally, it is expected that the patient will want to assume some measure of personal control over operations of the apparatus of the invention. Therefore, the apparatus of the invention allows partial care giver intervention as an option, although a fully preprogrammed operation is additionally part of the invention.

More specifically, and in accordance with primary objects and purposes of the invention, the apparatus for patient care and cleaning includes a set of semi-disposable pants with connection fittings for inflow and outflow hoses. The pants are provided with a recess portion for disposable absorbent, with sealing rings facilitating airflow for creation of a tight seal between the pants and the body of the patient. The pants are supplied with inflatable chambers for sealing particular areas of the body during excretory functions and washing process. The sensors installed within the wearing sections detect excretion and initiate patient care processes and disposing of the waste products. The mattress is provided with inflatable chambers that facilitate positioning of the patient body and creation of a hollow space for bath water, thereby facilitating in-bed bathing of the entire body.

BRIEF DESCRIPTION OF DRAWINGS

Other objects, features, and advantages of the present invention will be more apparent from the detailed description of the preferred embodiment of the invention which follows, when considered in light of the accompanying drawings, in which.

DETAILED DESCRIPTION OF THE INVENTION

Figure 1:
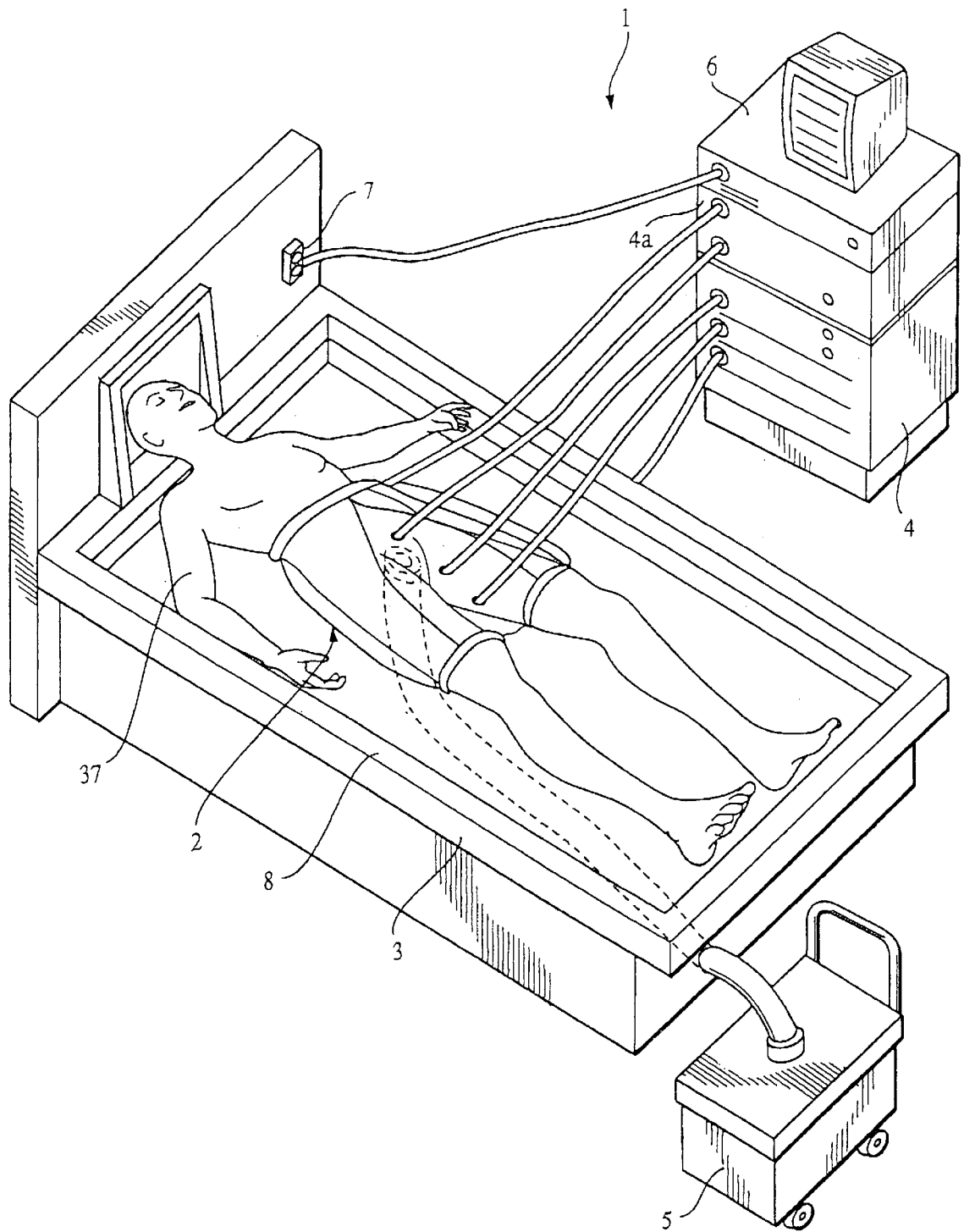
FIG. 1 is a perspective view schematically illustrating the state and use of the apparatus of the invention for patient care and cleaning, in which semi-disposable pants are fitted to the patient.
Figure 2:
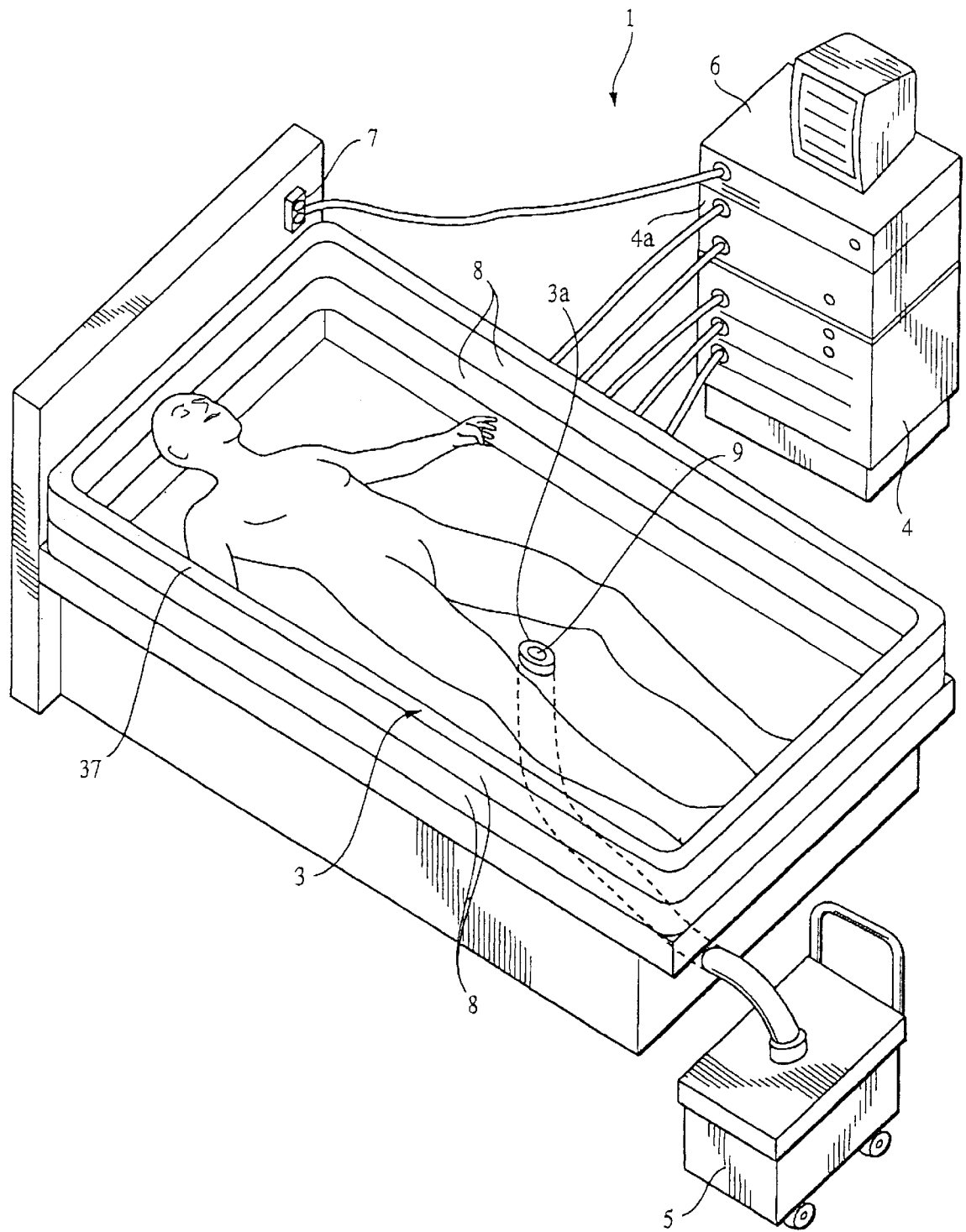
FIG. 2 is a perspective view schematically illustrating the state and use of the apparatus of the invention for patient care and cleaning, in which a patient uses the mattress of the invention.

FIGS. 1 and 2 depict two states of an embodiment of the apparatus 1 of invention for patient care and cleaning attached to a patient 37. The apparatus includes semi-disposable pants 2 (FIG. 1), a mattress 3, a wash liquid preparation unit 4, an air preparation unit 4a, a waste container 5, a control unit 6, and a remote control 7.

FIG. 2 depicts a second state of the embodiment of the apparatus 1, whereby the patient 37 is without the pants and the mattress 3 has a bath-shaped form with boards 8 for patient washing and care. In this state a plug 9 seals the out-flow opening 3a in the mattress 3.

Figure 3:
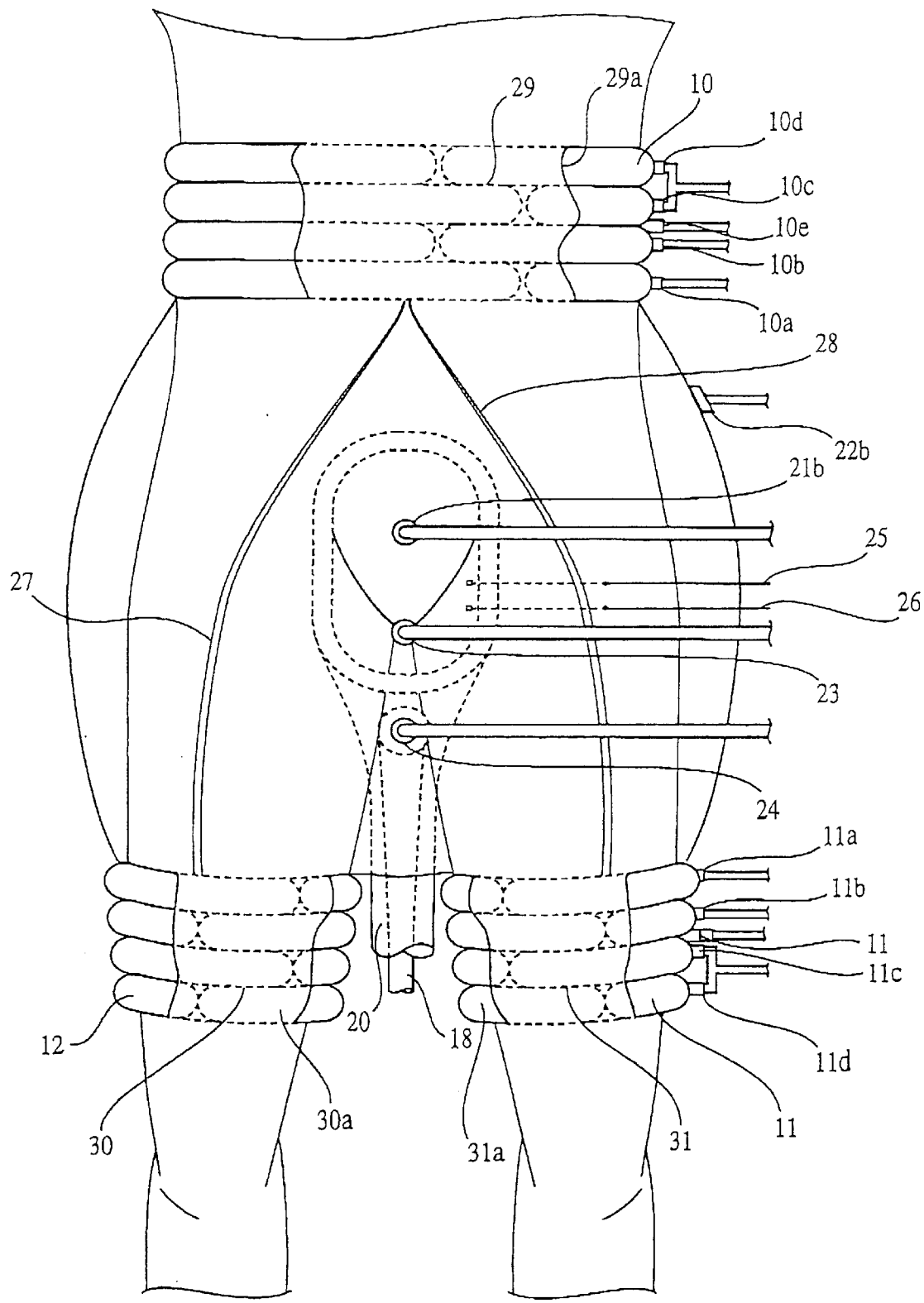
FIG. 3 is a perspective view schematically illustrating semi-disposable pants on the patient in the enclosed condition according to the present invention.
Figure 4:
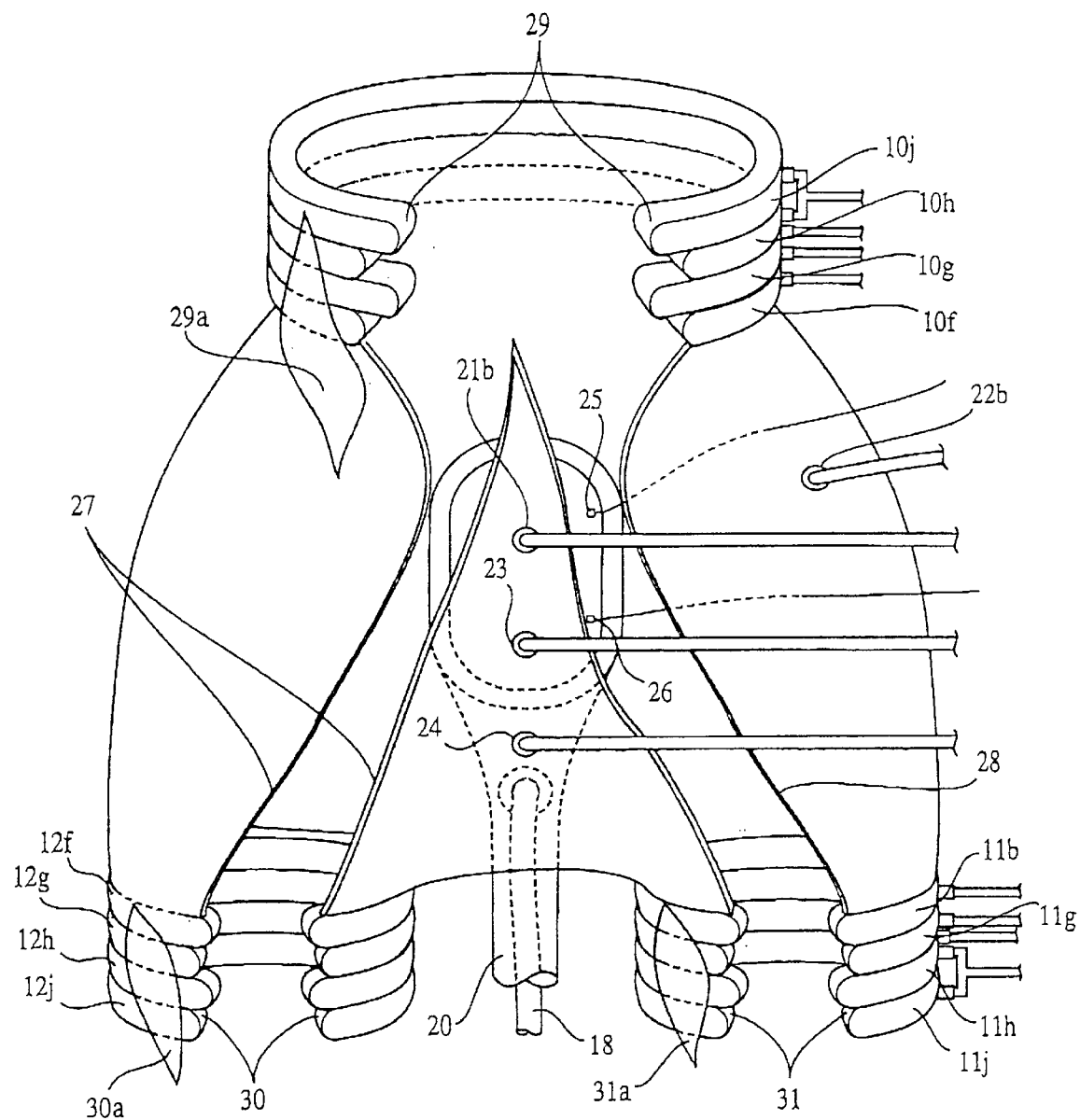
FIG. 4 is a perspective view schematically illustrating semi-disposable pants in an open condition according to the present invention.
Figure 5:
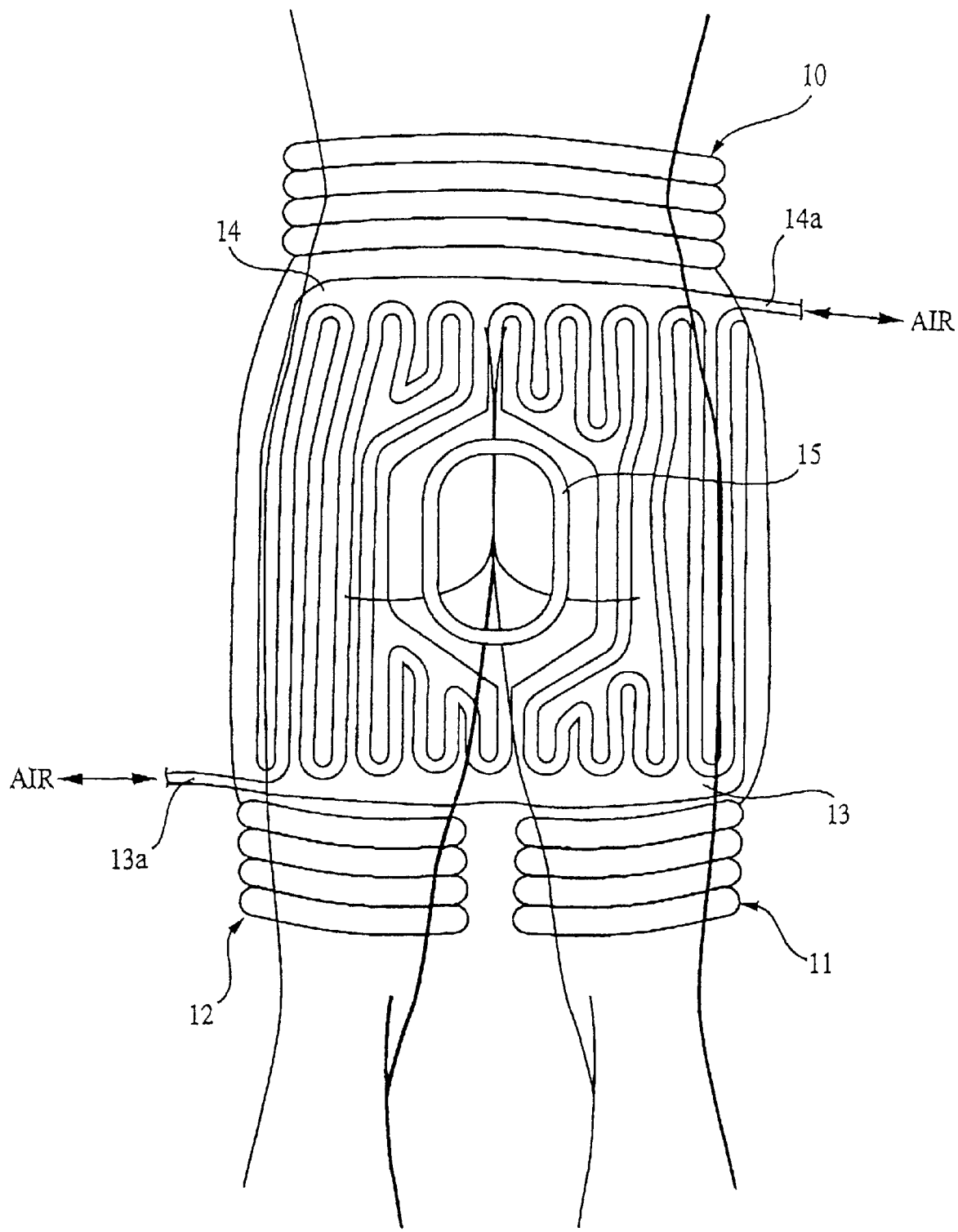
FIG. 5 is a rear view schematically illustrating the semi-disposable pants which have preprogrammed inflatable chambers on the lower back side according to the present invention.
Figure 6:
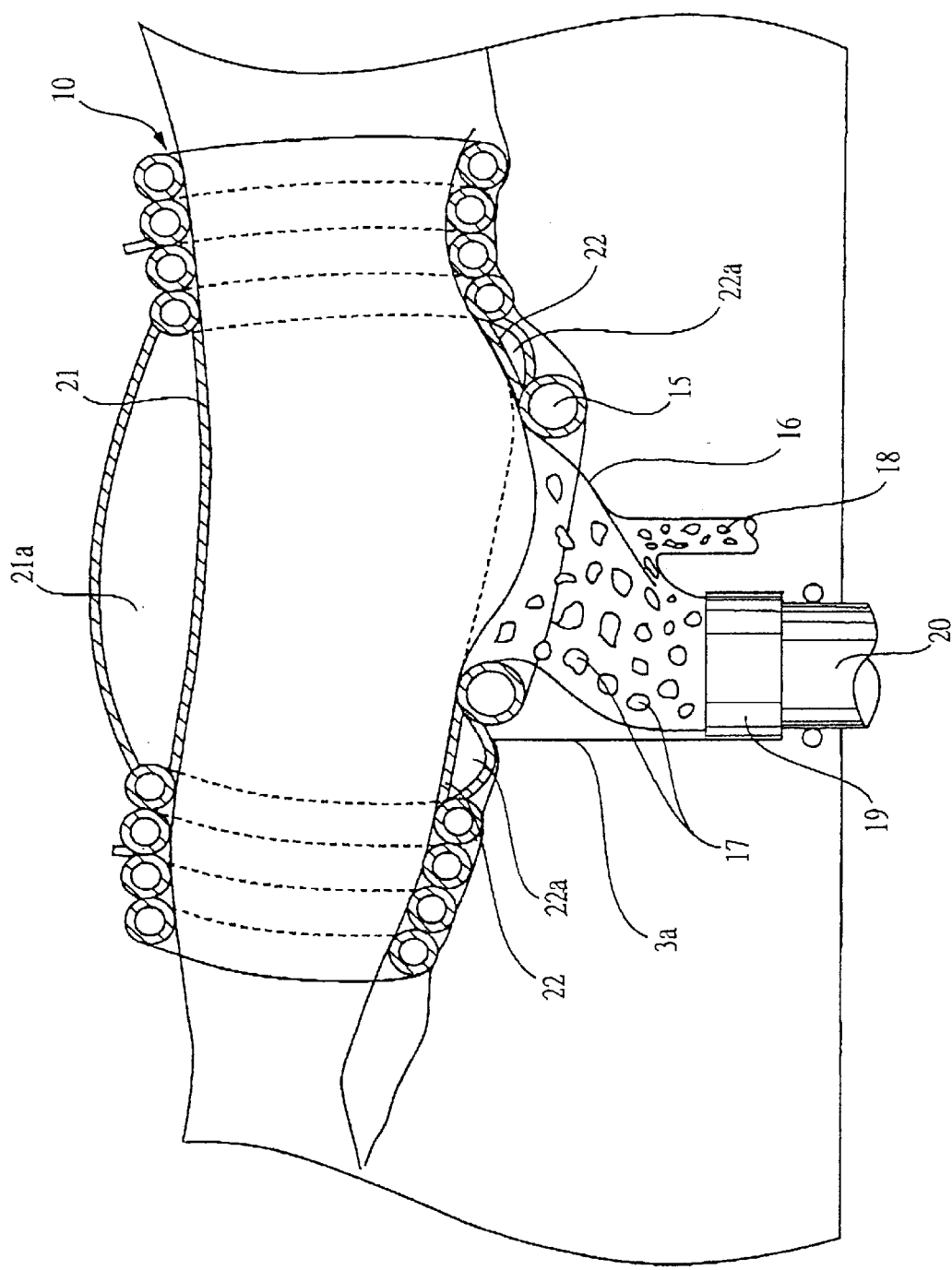
FIG. 6 is a cross-sectional view of the schematically presented canals and tubes for controlling air flow next to the skin for air flow enhancement and prevention of bed sores and providing a smooth material in pubic and anal regions for easy handling of excrement.
Figure 7:
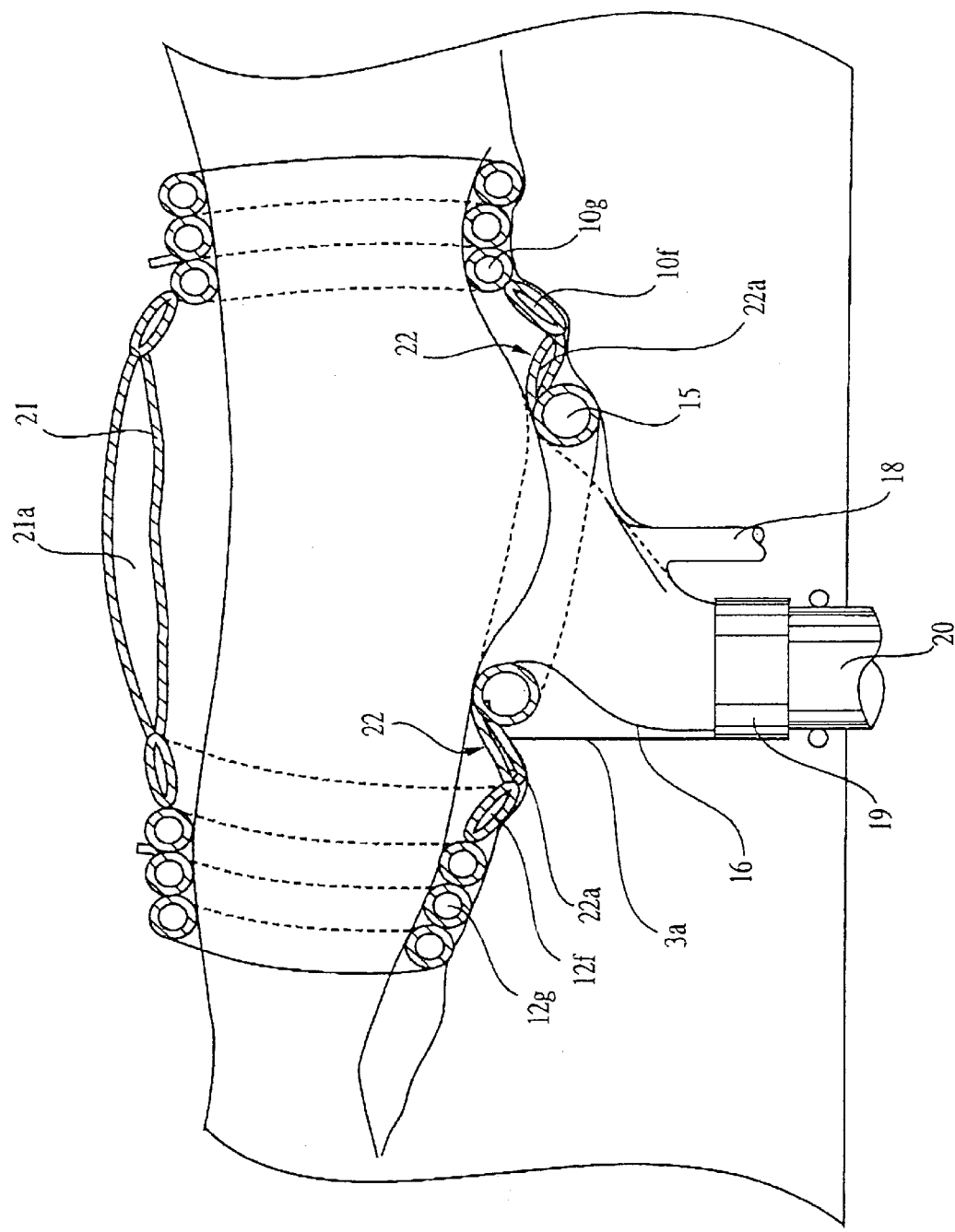
FIG. 7 is a schematic cross-sectional view showing the first state of the sealing rings with air supply attached to the semi-disposable pants during the washing of the patient's body.
Figure 8:
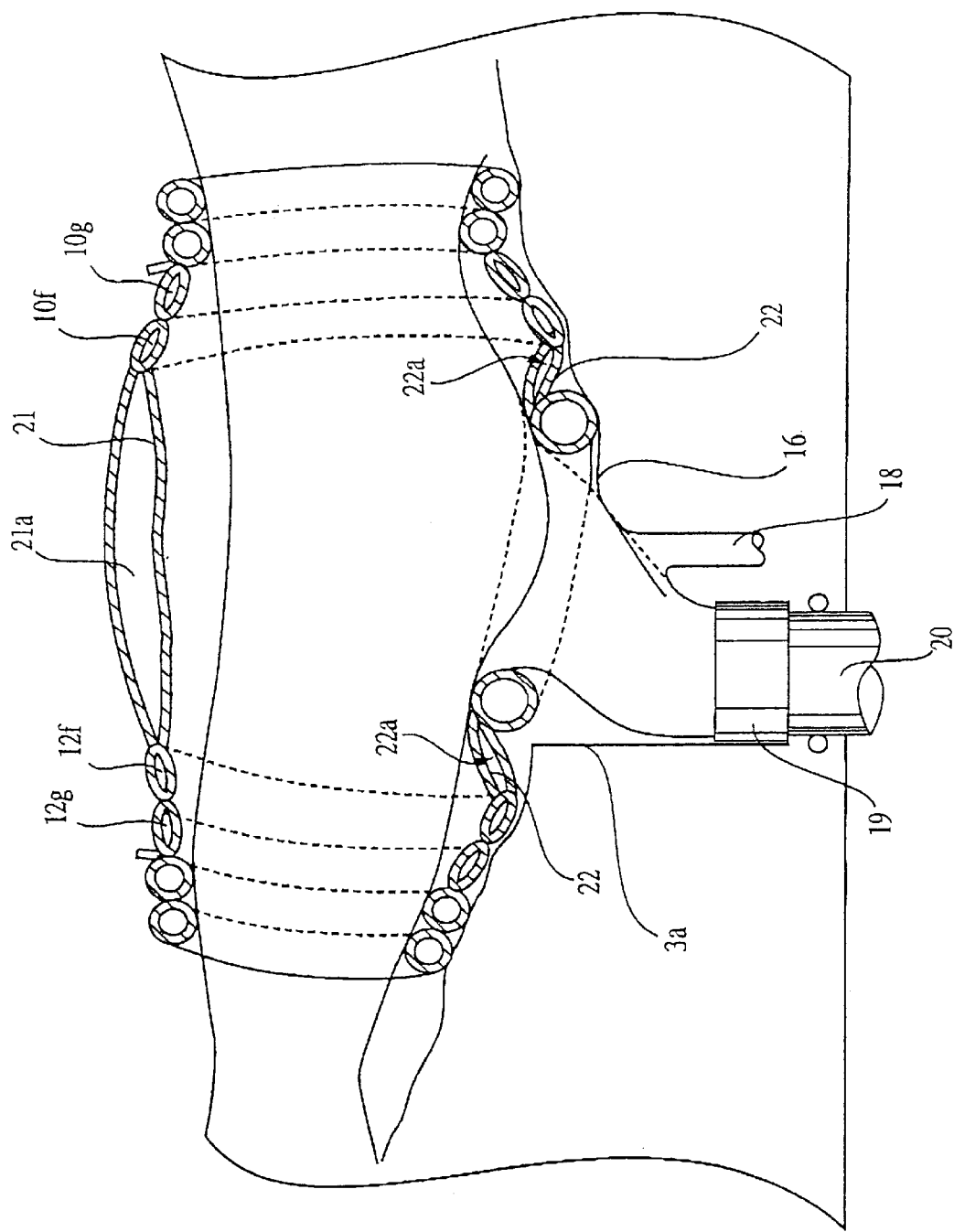
FIG. 8 is a schematic cross-sectional view showing the second state of the sealing rings of the semi-disposable pants during the washing and drying of the patient's body.
Figure 9:
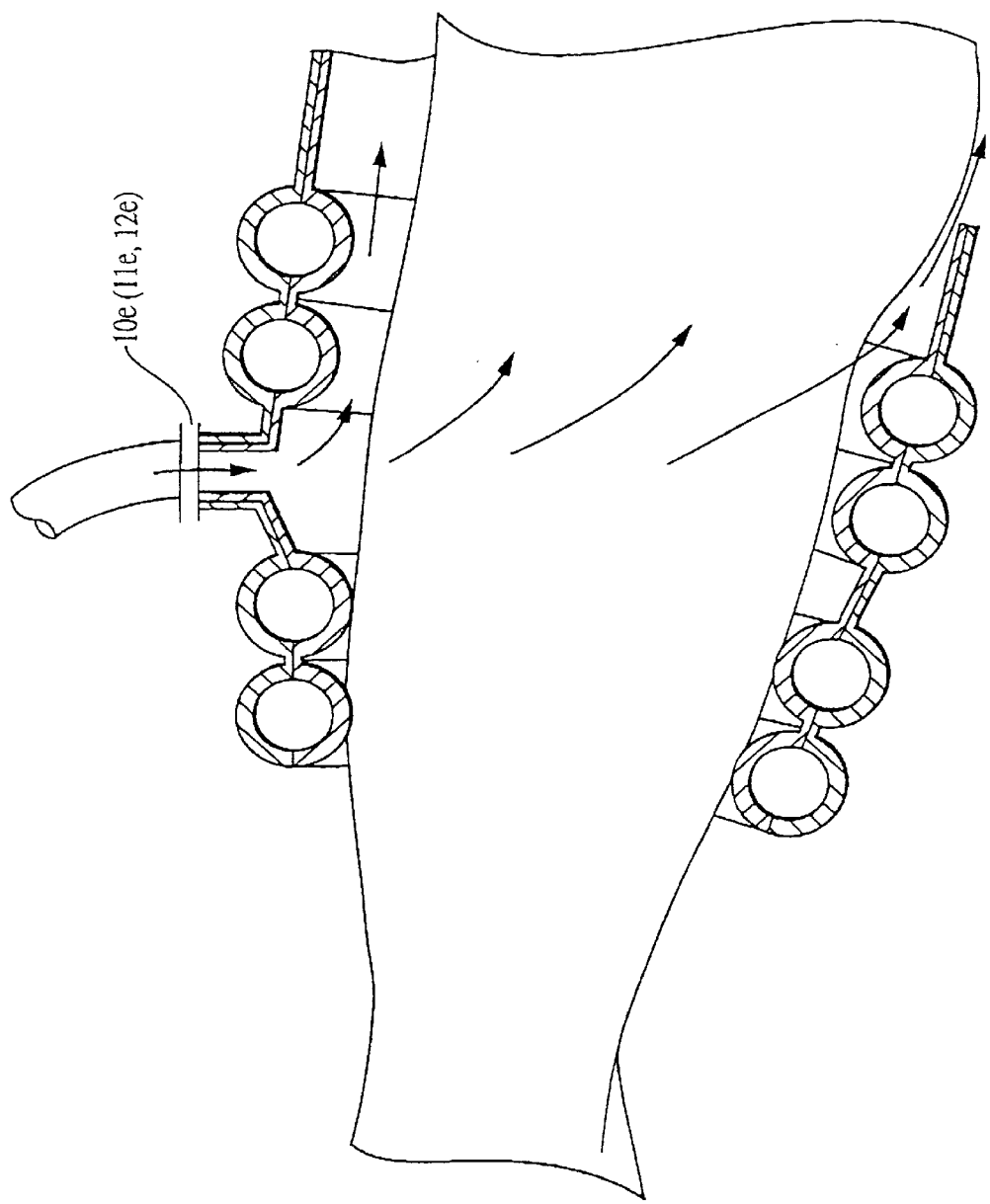
FIG. 9 is a cross-sectional detailed view, schematically showing the second state of the sealing rings of the semi-disposable pants during the washing and drying of the patient's body.

As shown in FIGS. 3–9, the pants 2 has two three groups 10, 11, 12 of sealing rings in the waist and femoral regions of the patient's body. The pants 2 with ring groups 10–12 are made of a flexible film, for example, such as polyethylene, polyvinyl chloride, etc. The sealing ring groups 10–12 are provided with connection fittings 10a–10d, 11a–11d, 12a–12d for inflow/outflow air pipes. There are connection fittings 10e 12e between rings inside the groups 10–12 for inflow air pipes. These connection fittings 10e–12e are seen best in FIG. 9. As best seen in FIG. 5, the back region of the pants 2 is provided with two groups 13, 14 of chambers and, in turn, they have connection fittings 13a, 14a for inflow/outflow air pipes. Moreover, the back region has an inflatable ring 15 for a framed recess portion 16 (see FIGS. 6–8) for providing a material discharge area for the apparatus 1. As shown in FIG. 6, the recess portion 16 is preferably filled with a disposable absorbent 17 made of small fractions of toilet paper, for example, or other suitable material. The absorbent material 17 is preferable soluble, or able to disintegrate in water. Absorbent material 17 is supplied through connection fitting 18. Recess portion 16 is provided with a connection fitting 19 for an outflow pipe 20 for waste materials including the absorbent 17. Pipe 20 passes through the hole 3a in the mattress 3.

As shown in FIGS. 3, 4 and 6, inflatable chambers 21a, 22a are provided with connection fittings 21b, 22b for inflow/outflow air pipes. Moreover, the pants 2 are provided with a connection fitting 23 for an inflow pipe for washing materials, such as warm water, soap, antiseptic, lotion, etc.

and a connection fitting 24 for an inflow pipe with warm air for drying of the patient's body, and the supply of powder, if desired. Also, sensors 25, 26 are provided on the inner side of the pants 2 for measuring environmental data, such as humidity, gas emission (methane, sulfur, etc.) and others, such as gas consistency, temperature, and gas pressure. The pants 2 are further provided with fasteners 27–31 for comfortable dressing and undressing, and for the manual care of the patient 37. Therewith, the fasteners 27, 28 are pressure-sealing fasteners in the closed condition (see FIG. 3). The fasteners 29, 30, 31 have a self-gripping fastening system 29a, 30a, 31a (made of hook and loop fasteners) that secure the groups 10, 11, 12 of sealing rings in the closed position with a specific diameter according to the patient's body. In turn, the sealing rings 10f, 10g, 10h, 10j; 11f, 11g, 11h, 11j; and 12f, 12g, 12h, 12j are shifted relative to each other (see FIG. 4) in order to seal the borders of the shifted sealing rings.

Figure 10:
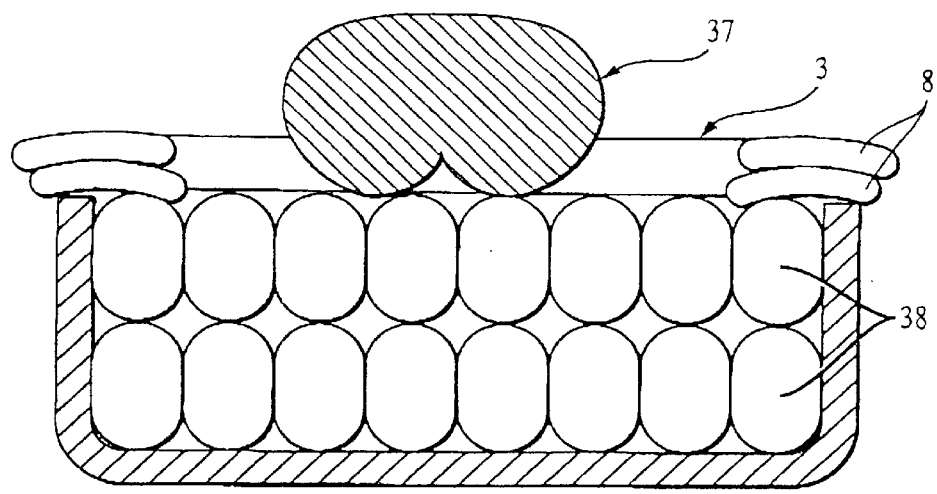
FIG. 10 is a schematic cross-sectional view showing the state of the mattress when the patient is lying on his back.

As shown in FIGS. 1 and 10, the air has been released from the boards 8 of the mattress 3 and the mattress 3 has assumed a predetermined form with inflated chambers 3b.

Figure 11:
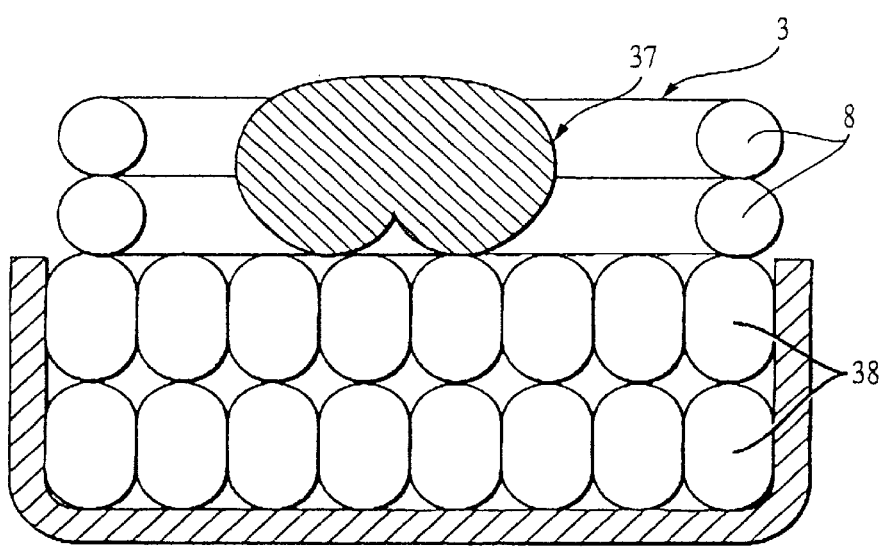
FIG. 11 is a schematic cross-sectional view showing the state of the mattress in position creating a bath around the stretched-out patient's body.

FIGS. 2 and 11 illustrate a bath-shaped form of the mattress with inflated chambers 3b and 8.

Figure 12:
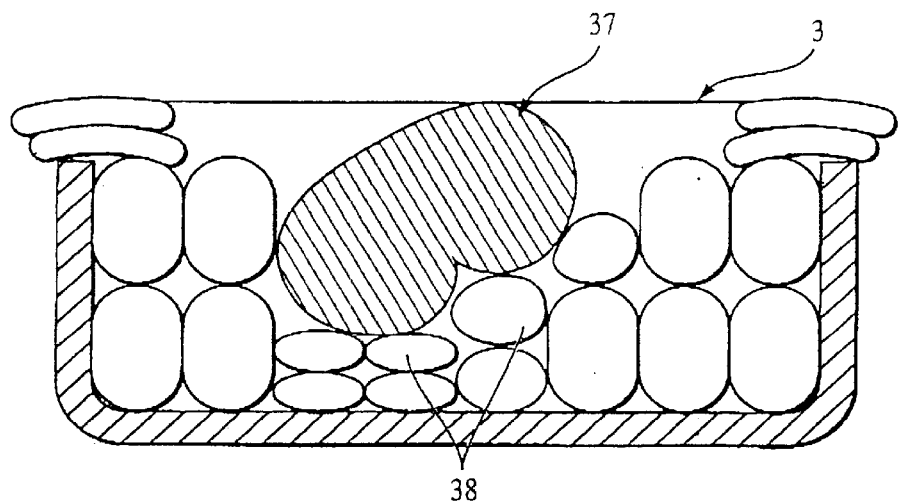
FIG. 12 is a schematic cross-sectional view showing the state of the mattress when the patient is lying on his side.

FIG. 12 illustrates the state in which some air chambers 3b are inflated and others deflated for turning over the patient 37. The same possibility (not shown) is available in the state of the bath-shaped form of the mattress 3.

With reference again to FIGS. 1 and 2, the wash liquid preparation unit 4, the air preparation unit 4a, the waste container 5, and the control unit 6 are connected to the pants 2 and the mattress 3 by various pipes and cables. The remote control 7 is displaced close to the patient 37.

Figure 13:
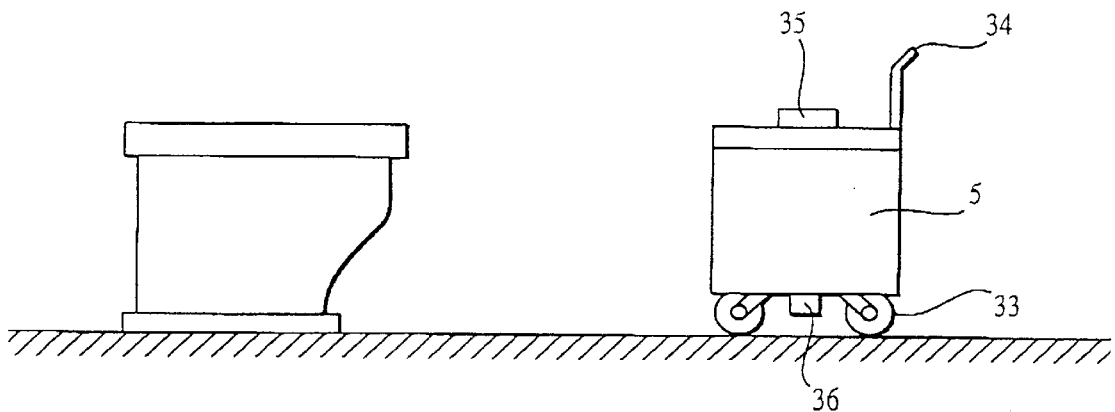
FIG. 13 is a schematic cross-sectional view showing the use of the waste collection container, near the water closet, according to the invention.
Figure 14:
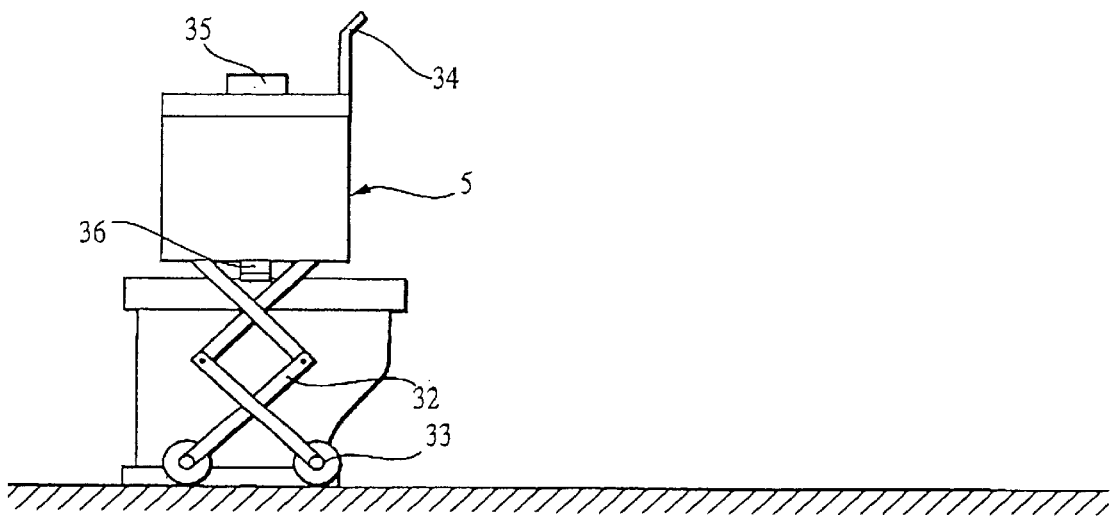
FIG. 14 is a schematic cross-sectional view showing the state of use of the waste collection container above the water closet, according to the invention.
Figure 15:
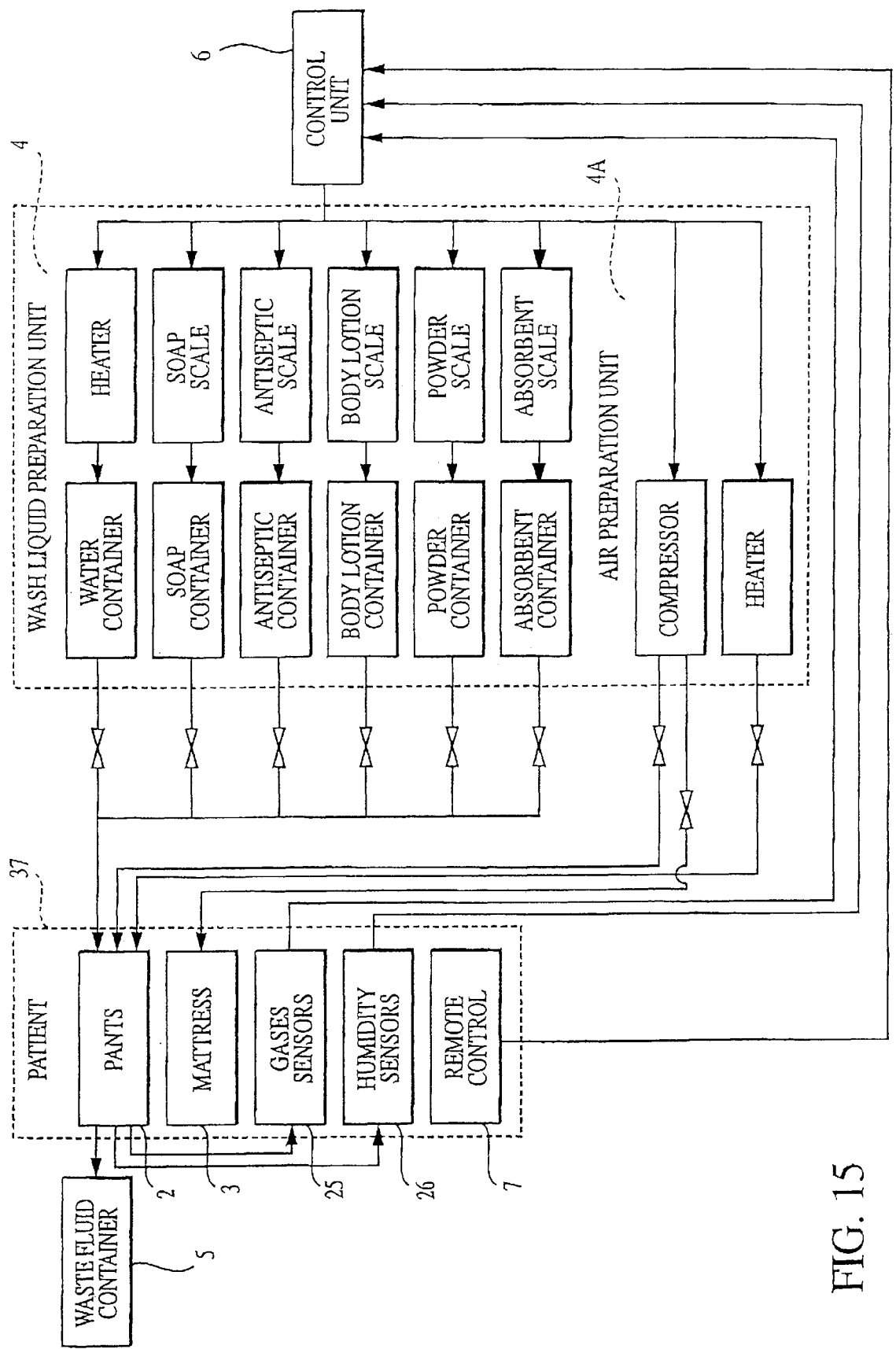
FIG. 15 is a diagram generally illustrating the principal interactions between major components of the invention.

As shown in FIGS. 13 and 14, the waste container 5 has a lifter 32 supported on wheels 33, a handle 34, a connection fitting 35 for an inflow waste materials hose, and a discharge valve 36. FIG. 14 illustrates an elevated position of the waste container 5 for discharging through the open valve 36 into a water closet or other appropriate container.

The apparatus described above operates as follows. First, the patient 37 is dressed in underwear (not shown), such as panties with a hole in the anal and pubic regions. This underwear can be made of thin cotton textile, such as batiste, for example. The open pants 2 (see FIG. 4) are fitted on the patient 37 and closed by the fasteners 27–31. The pipes and cables are connected with appropriate connection fittings (see FIG. 1). The inflow materials preparation unit 4 and control unit 6 are preprogrammed and switched on.

At the beginning of catharsis and/or urination gas and/or humidity sensors 25, 26 give information to the control unit 6. In turn, the air preparation unit 4a inflates three groups 10–12 of sealing rings and the chambers 21a, 21b. Thus, all regions of the patient's body inside the pants 2 are sealed and the bulk of the excrement and urine is kept near the anal and pubic regions. Concurrently, two groups 13, 14 of chambers are deflated. It is significant that the solid excrement hitting into the recess portion 16 are dominantly encapsulated in the pieces of absorbent 17 and, in so doing, the smearing of the patient's body is reduced. Then, waste material is removed from the recess portion 16 into the waste container 5.

After catharsis and/or urination, the warm washing water and soap are fed from the wash liquid preparation unit 4 and are injected into the crotch region. Simultaneously, the chambers 21a, 22a are deflated and the region to be washed expanded. At the same time, by means of alternate inflating and deflating of two groups 13, 14 of chambers and the injection of warm air through fittings 10e–12e, 24, the washing process is enhanced. The washing region is gradually extended to eventually encompass the entire soiled area. The air from the sealing rings 10f–12f and 10g–12g in the groups 10–12 is sequentially released through fittings 10a–12a and 10b–12b and, in so doing, so the washing region gradually increases from dirtier to cleaner places. Finally, it is preferred that the rinsing water is injected with a dose of body lotion.

After the washing cycle is complete, air in all of the sealing rings in groups 10–12 is completely released, warm air is then injected, and an alternate inflation and deflation of groups 13, 14 of the pants chambers is continued to effect some body massage and to make the drying process more pleasurable. Preferably, powder is then injected one or more times during the drying and ventilation cycles. A new dose of disposable absorbent 17 is inserted in the recess portion 16. The ventilation cycle is continued in the interval between catharsis and/or urination.

All above-mentioned cycles may be actuated or terminated by remote control.

Pipes and cables are disconnected from connection fittings and the patient is undressed if washing and care of the entire body is intended. The opening 3a in the mattress 3 is tightly closed with the plug 9. The boards 8 are inflated and the mattress-bath is filled with wash water.

For turning over the mattress, chambers 3b close to the patient's body are completely or partially deflated and the process is manually guided using control unit 6 or the remote control 7.

As an alternative to the gravity discharge for the removal of waste material from the pants, or trousers, it is contemplated that a vacuum removal could be provided. For this purpose, a vacuum pump would be provided for removal of such waste material into a container under the patient's bed. A particular benefit of the vacuum in the trousers is that it facilitates the air flow between the sealing rings, groups 10–12, and the patient's body. Sick, old, and frail patients often have a very low venal pressure. If any pressure on the skin is applied, this may stop circulation. Having a vacuum, or relatively low pressure, in the trousers, air pressure can be minimized or eliminated altogether. A vacuum or low pressure on the skin actually can help blood vessels expand near the skin and improve localized circulation there.

It is also contemplated to employ a second vacuum pump to remove the effluent from the tank under the patient's bed to a collecting tank. In the collecting tank, the material can then be sterilized and, for example, made ready to enter the municipal sewer system.

What is claimed is:

1. An apparatus for patient care and cleaning, said apparatus comprising:
    pants for covering a portion of a patient's body, said pants being provided with connection fittings for connection of an inflow pipe and an outflow pipe, said pants having a hollow space in a discharge region for effluent material;
    said pants further comprising sealing rings for surrounding waist and femoral regions of the patient for selective sealing and unsealing of a space inside said pants through determinate patient care cycles using air flow for lowering pressure required for creating a seal;
    said pants further comprising an inner surface providing inflatable chambers for selective sealing and unsealing all surfaces of a patient's body positioned within said pants except pubic and anal regions during excretory functions and said patient care cycles;
    said pants further comprising manually operated pressure-sealing fasteners for optional care giver control of in-pant environment during said patient care cycles;
    sensors positioned within said pants for environmental monitoring and for control of said patient care cycles;
    a mattress provided with inflatable chambers for positioning the patient's body, said mattress further being provided with inflatable chambers for creating a bath-shaped basin for bathing an entirety of the patient's body while positioned upon said mattress;
    a care materials inflow preparation unit for delivery of care materials through said inflow pipes to said patient's body positioned within said pants; and
    a control unit for receiving information from said sensors and controlling said patient care cycles.

2. An apparatus according to claim 1, wherein said care materials inflow preparation unit comprises means for heating, scaling, mixing, transforming, and transporting of said care materials.

3. An apparatus according to claim 1, further comprising a waste container for collecting effluent waste material from said discharge area of said pants and for transporting said materials to a waste water disposal system.

4. An apparatus according to claim 3, wherein said connection fittings are provided with quick-coupling devices for quick response to patient need for mobility and facilitating hook-up of said care materials inflow preparation unit, said waste container, and said control unit while the patient is in a lying, standing, or seated position.

5. An apparatus according to claim 3, wherein said waste container is provided with wheels, a handle, and a hoisting means for elevation of said container above a water closet for disposal of said waste.

6. An apparatus according to claim 1, wherein said control unit comprises a remote control device for optional manual activation by said patient of said patient care cycles.

7. An apparatus according to claim 1, wherein said patient care cycles include a washing process and a drying process, and said inflatable chambers of said pants and/or said mattress are preprogrammed in said control unit for inflation and deflation for enhancement of said washing and drying processes.

8. An apparatus according to claim 1, further comprising a source of loose absorbent material and a connection between said source and said hollow space.

9. An apparatus according to claim 8, wherein said loose absorbent material comprises a water-soluble or disintegratable material.

10. An apparatus according to claim 1, wherein said patient care cycles includes a washing process, and said sealing rings in the waist region of the patient comprise groups of sequentially inflatable hoses for facilitating said washing process.

11. An apparatus according to claim 1, wherein said sensors include measurement of humidity, gas emission, gas consistency, temperature, and gas pressure.

12. A method of cleaning a bed-ridden patient comprising:
    covering a portion of a patient's body with pants, said pants being provided with connection fittings for connection of an inflow pipe and an outflow pipe, said pants having a hollow space in a discharge region for effluent material, said pants further including a plurality of inflatable sealing rings surrounding waist region of the patient and a plurality of inflatable sealing rings surrounding said femoral regions of the patient, said pants further including an inner surface providing inflatable chambers for selective sealing and unsealing all surfaces of a patient's body positioned within said pants except pubic and anal regions during excretory functions and said patient care cycles;

placing the patient on a mattress provided with inflatable chambers for positioning the patient's body, said mattress further being provided with inflatable chambers for creating a bath-shaped basin;

inflating said sealing rings at said waist and femoral regions of the patient's body to seal a space around the patient's body between said waist and femoral regions, and inflating said chambers of said pants between said waste and femoral regions;

injecting washing liquid into said space around the patient's body through said inflow pipe and removing effluent through said outflow pipe.

13. A method according to claim 12, further comprising:

simultaneously with said inflating of said sealing rings at said waist and femoral regions of the patient's body and the injecting of washing liquid into said space around the patient's body, deflating said chambers of said pants and injecting air into said space to enhance the cleaning of the patient's body.

14. A method according to claim 12, further comprising:

during said injecting of said washing liquid into said space around the patient's body, expanding the extent of said space around the patient's body between said waist and femoral regions by deflating at least one of said sealing rings at said waist or femoral regions of the patient; and injecting rinsing water to said expanded space.

15. A method according to claim 14, further comprising:

injecting warm air into said expanded space.

16. A method according to claim 14, further comprising:

alternately inflating and deflating said inflatable chambers to effect body massage to the patient.

17. A method according to claim 14, further comprising:

injecting body lotion with said rinsing water.

18. A method according to claim 15, further comprising:

injecting powder during said injecting of warm air.

\* \* \* \* \*